United States Patent
Brugger et al.

(10) Patent No.: US 7,544,300 B2
(45) Date of Patent: Jun. 9, 2009

(54) BATCH FILTRATION SYSTEM FOR PREPARATION OF STERILE FLUID FOR RENAL REPLACEMENT THERAPY

(75) Inventors: James M. Brugger, Newburyport, MA (US); Jeffrey H. Burbank, Boxford, MA (US); Brian C. Green, Westford, MA (US)

(73) Assignee: NxStage Medical, Inc., Lawrence, MA (US)

( * ) Notice: Subject to any disclaimer, the term of this patent is extended or adjusted under 35 U.S.C. 154(b) by 0 days.

(21) Appl. No.: 11/160,764

(22) Filed: Jul. 7, 2005

(65) Prior Publication Data

US 2007/0007208 A1 Jan. 11, 2007
US 2008/0053905 A9 Mar. 6, 2008

Related U.S. Application Data

(63) Continuation of application No. PCT/US2004/000476, filed on Jan. 7, 2004.

(60) Provisional application No. 60/438,567, filed on Jan. 7, 2003.

(51) Int. Cl.
  *B01D 61/30* (2006.01)
  *B01D 61/00* (2006.01)

(52) U.S. Cl. .......... 210/645; 210/97; 210/143; 210/646; 210/739; 210/767; 604/4.01; 604/5.01; 604/6.09; 604/6.11; 604/6.13; 604/9; 604/28; 604/29; 604/30

(58) Field of Classification Search .......... 210/97, 210/143, 645, 646, 739, 767; 604/6.09, 6.11, 604/6.13, 9, 28, 29, 30, 4.01, 5.01
See application file for complete search history.

(56) References Cited

U.S. PATENT DOCUMENTS

| 4,059,512 | A |   | 11/1977 | Harris |
| 4,370,983 | A | * | 2/1983 | Lichtenstein ............... 600/301 |
| 4,711,715 | A | * | 12/1987 | Polaschegg ............... 210/103 |
| 5,308,333 | A |   | 5/1994 | Skakoon |
| 5,536,412 | A |   | 7/1996 | Ash |
| 5,622,626 | A |   | 4/1997 | Matkovich et al. |

(Continued)

FOREIGN PATENT DOCUMENTS

| DE |   | 8305713 |   | 12/1985 |
| DE |   | 19704564 |   | 8/1998 |
| GB |   | 2135598 | A * | 9/1984 |
| WO | WO 96/036370 |   | 11/1996 |

(Continued)

*Primary Examiner*—John Kim
(74) *Attorney, Agent, or Firm*—Miles & Stockbridge PC; Mark A. Catan (57) ABSTRACT

A method and device for blood treatments that use fluids such as dialysate and replacement fluid for renal replacement therapy. In an embodiment, fluid is passed either by pump or passively by gravity feed, through a microporous sterilization filter from a fluid source to a replacement fluid container. The latter forms a batch that may be used during treatment. The advantage of forming the batch before treatment is that the rate of filtering needn't match the rate of consumption during treatment. As a result, the sterilization filter can have a small capacity. In another embodiment, a filter is placed immediately prior to the point at which the sterile fluid is consumed by the treatment process. The latter may be used in combination with the former embodiment as a last-chance guarantee of sterility and/or that the fluid is free of air bubbles. It may also be used as the primary means of sterile-filtration.

4 Claims, 11 Drawing Sheets

U.S. PATENT DOCUMENTS

| | | | |
|---|---|---|---|
| 5,645,734 | A | 7/1997 | Kenley et al. |
| 5,702,597 | A | 12/1997 | Chevallet et al. |
| 5,779,905 | A | 7/1998 | Morandi et al. |
| 5,919,357 | A * | 7/1999 | Wilkins et al. ............. 210/120 |
| 5,972,225 | A | 10/1999 | Karras et al. |
| 6,132,616 | A | 10/2000 | Twardowski et al. |
| 6,187,207 | B1 | 2/2001 | Brauer |
| 6,253,567 | B1 | 7/2001 | Imanari et al. |
| 6,254,567 | B1 | 7/2001 | Treu et al. |
| 6,287,516 | B1 | 9/2001 | Matson et al. |
| 6,331,252 | B1 | 12/2001 | El Sayyid et al. |
| 6,582,385 | B2 | 6/2003 | Burbank et al. |
| 6,589,482 | B1 | 7/2003 | Burbank et al. |
| 6,626,857 | B1 * | 9/2003 | Ohta et al. ................ 604/6.13 |
| 6,649,063 | B2 * | 11/2003 | Brugger et al. ............ 210/650 |
| 6,830,553 | B1 | 12/2004 | Burbank et al. |
| 6,855,122 | B1 * | 2/2005 | Ohta et al. ................ 604/6.13 |
| 7,214,312 | B2 | 5/2007 | Brugger et al. |
| 7,226,538 | B2 | 6/2007 | Brugger et al. |
| 2001/0048909 | A1 | 12/2001 | Taylor |
| 2003/0130606 | A1 | 7/2003 | Tuck |
| 2004/0045881 | A1 * | 3/2004 | Collins et al. ............... 210/101 |
| 2004/0069709 | A1 * | 4/2004 | Brugger et al. ............. 210/646 |
| 2004/0089594 | A1 | 5/2004 | Collins et al. |
| 2005/0045548 | A1 | 3/2005 | Brugger et al. |
| 2005/0209547 | A1 * | 9/2005 | Burbank et al. ........... 604/5.01 |
| 2007/0007208 | A1 | 1/2007 | Brugger et al. |
| 2007/0038191 | A1 | 2/2007 | Burbank et al. |
| 2007/0260168 | A1 | 11/2007 | Brugger et al. |
| 2008/0053905 | A9 | 3/2008 | Brugger et al. |
| 2008/0203023 | A1 | 8/2008 | Burbank et al. |

FOREIGN PATENT DOCUMENTS

| | | |
|---|---|---|
| WO | WO 03/006100 | 1/2003 |
| WO | WO 03/006139 | 1/2003 |
| WO | WO 03/103533 | 12/2003 |
| WO | WO 2004/062710 | 7/2004 |
| WO | WO 2004/066121 | 8/2004 |
| WO | WO 2005/068043 | 7/2005 |

* cited by examiner

Fig. 16

BATCH FILTRATION SYSTEM FOR PREPARATION OF STERILE FLUID FOR RENAL REPLACEMENT THERAPY

CROSS REFERENCE TO RELATED APPLICATIONS

The present application is a continuation of the prior PCT application PCT/US04/00476, filed Jan. 7, 2004, which claims the benefit of U.S. Provisional Application No. 60/438,567 filed Jan. 7, 2003.

BACKGROUND OF THE INVENTION

During hemofiltration, hemodialysis, hemodiafiltration, ultrafiltration, and other forms of renal replacement therapy, blood is drawn from a patient, passed through a filter, and returned to the patient. Depending on the type of treatment, fluids and electrolytes are exchanged in the filter between a dialysate and/or extracted from the blood by filtration. One effect may be a net loss of fluid and electrolytes from the patient and/or exhaustion of dialysate, with a concomitant need for its replenishment, again depending on the type of treatment. To replace fluid lost from the patient and keep the patient from dehydrating, replacement fluid may be injected into the patient at a rate that matches a rate of loss, with an adjustment for a desired net change in the patient's fluid complement. To replace exhausted dialysate, fresh dialysate is continuously circulated through the filter.

Conventionally, dialysate and/or replacement fluid is supplied from either of two sources: batches of fluid, typically in multiple bags, or a continuous source of water that is sterile-filtered and added to concentrated electrolytes to achieve the required dilution level. Because replacement fluid is injected directly into the patient, replacement fluid must be sterile. When either method is used to generate replacement fluid, there is a risk of contamination of the fluid. Contamination may occur, for example, at the point where bags of fluid are accessed ("spiked") or at any connection in the fluid circuit linking the source to the patient.

In many instances, such therapies may require a large quantity of sterile fluid. A typical way to provide the large quantity of replacement fluid is to provide multiple bags of replacement fluid, dialysate, or infusate. The connection of these bags of fluid to an extracorporeal blood circuit, there is a risk of touch-contamination resulting in the introduction of biological contaminants into the fluids. Presently, methods of producing large volumes of dialysate from tap water are known, but each requires complex water purification and standardization equipment, since impurities and cleaning additives such as chlorine vary greatly in tap water from municipality to municipality and within a municipality over time. (See Twardowski U.S. Pat. Nos. 6,146,536 and 6,132,616.) Moreover, dialysate solution, whether prepared online or prepackaged, while of the proper concentration for use as a sterile replacement fluid, never enters the patient's body. Instead, dialysate flows past a semipermeable membrane that permits ions to be exchanged across the membrane until a balance between their concentrations in blood and their concentrations in the dialysis is achieved. This is effective to remove impurities from the blood and to add missing electrolytes to the blood. Because it does not have to be infused, dialysate is less expensive than solutions prepared as replacement fluids, which are injected directly into a patient.

Attempts to render dialysate sufficiently sterile for use as a replacement fluid in hemofiltration and hemodiafiltration have focused on continuous sterilization processes that require a separate dialysate filtration/purification apparatus that must be periodically purged and verified to provide sufficient constant flow of sterile replacement fluid required for hemofiltration. (See Chavallet U.S. Pat. Nos. 6,039,877 and 5,702,597). Such devices are necessarily complicated and require separate pumping systems for the sterilization process. In addition, the rate of supply of dialysate for such systems is very high, requiring an expensive filter to be used. The same high-rate problem exists for the generation of replacement fluid for hemofiltration, and therefore also requires an expensive filter.

SUMMARY OF THE INVENTION

In the present invention, sterile replacement fluid or dialysate may be generated in batch form by sterile-filtering. According to embodiments of inventions disclosed, non-sterile fluid is passed through a filter prior to treatment to prepare a batch of replacement fluid. This process may be permitted to take any length of time because the rate of flow of non-sterile replacement fluid (or components thereof) through the filter is completely independent of the rate of consumption by the renal therapy. Because the filters used for sterile-filtering tend to be expensive, it may be desirable for such a batch process to employ a small filter for such filtration. Such a filter can have a flow capacity that is much lower than that required for real-time filtering of the replacement fluid (or components). In addition to preparation of sterile fluid from non-sterile fluid, embodiments of inventions disclosed may be used to sterilize already-sterile fluid as a precaution against touch contamination.

Generally replacement fluid is heated before being infused into a patient. This is often accomplished by heating the fluid as it is being infused with a heater with sufficient heating capacity. The capacity of the heater must be matched to the mass flow of the fluid and the temperature rise required. In a batch preparation process, where a batch of fluid is prepared over a substantial period before use, a small heater may heat the replacement fluid over a long period of time. Insulation may be provided to prevent heat loss. An insulating outer container for the sterile replacement fluid may be provided. For example, the container may be an insulated box with room for one or more large disposable sterile bags of the type normally used for infusible fluids.

The preparation of warm sterile replacement fluid may be automated by a control process that permits a user to set up the fluids and other materials well in advance of a scheduled treatment. The process would ensure that the replacement fluid is sterilized and heated to the proper temperature when the treatment is to begin.

The automation process may be permit the user to select how far in advance of the treatment the preparation should be performed. This may be useful, for example, where a particular source of replacement fluid has proved to release more than a usual quantity of dissolved gases upon heating. Heating the replacement fluid and permitting it to settle for a time before it is used may allow gases to come out of solution and settle at the top of the batch vessel or vessels. The automation process may be incorporated in the control functions of renal therapy machine.

The invention or inventions will be described in connection with certain preferred embodiments, with reference to the following illustrative figures so that it may be more fully understood. With reference to the figures, it is stressed that the particulars shown are by way of example and for purposes of illustrative discussion of the preferred embodiments of the present invention or inventions only, and are presented in the cause of providing what is believed to be the most useful and readily understood description of the principles and conceptual aspects of the invention or inventions. In this regard, no attempt is made to show structural details of the invention in more detail than is necessary for a fundamental understanding of the invention or inventions, the description taken with the drawings making apparent to those skilled in the art how the several forms of the invention or inventions may be embodied in practice.

DETAILED DESCRIPTION

Figure 1:
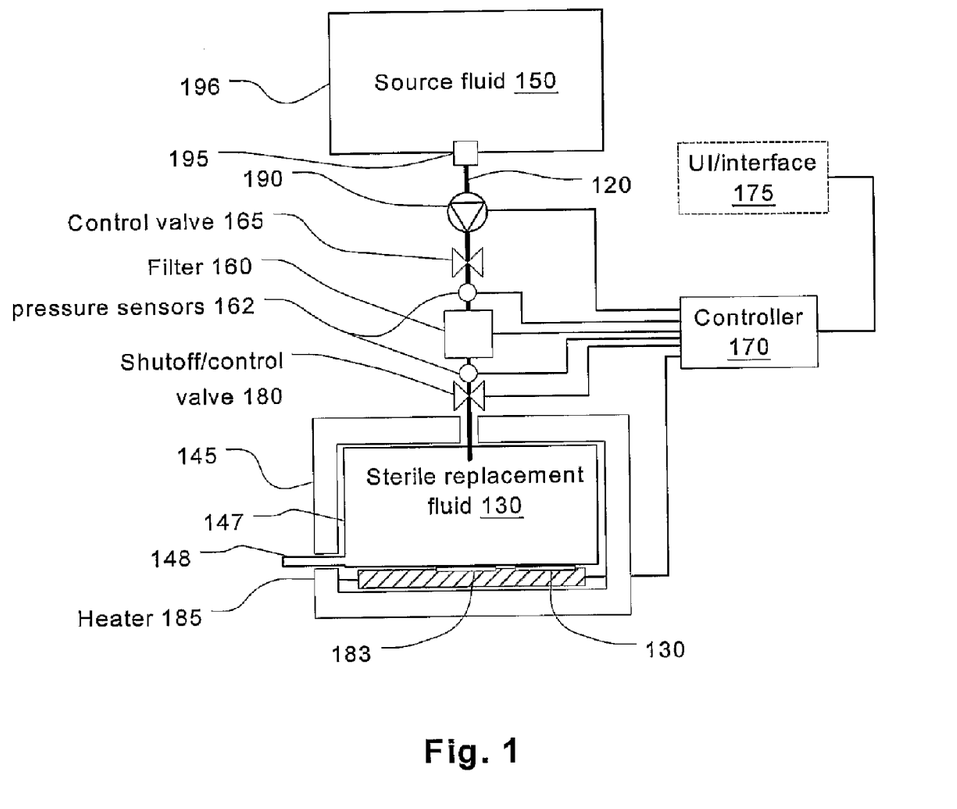
FIG. 1 is a schematic illustration of a standalone/retrofit apparatus system for batch filtration of a sterile replacement fluid.

Referring to FIG. 1, a filter 160 filters fluid from a source of fluid 150 to generate a batch of sterile replacement fluid 130. The filter 160 may be, and preferably is, a microporous filter that blocks all materials except dissolved electrolytes and water. Thus, the result of the filtration process is to sterilize the raw fluid from the source of fluid 150. The source of fluid 150 may be a container of sterile or non-sterile replacement fluid, one or more containers of constituents which, when combined, form a proper replacement fluid. Any of the latter may include a continuous source such as a water tap. One or more conduit elements form a line 120 to convey the source fluid 150 through the filter 160 and into a batch container 147.

The latter may be any type of sterile, preferably disposable container, for example, a large IV bag. It may also include a number of such containers appropriately interconnected to permit flow into and out of them in the fashion of container 147.

Included in the conveyance from source fluid 150 to sterile replacement fluid 130 may be a pump 190, such as a peristaltic pump. The pressure at an outlet of the filter 160 may be sensed by a pressure sensor 162 and the pump 190 controlled by a controller 170 to insure a predefined transmembrane pressure (TMP) threshold of the filter 160 is not breached. The TMP may be maintained at a maximum safe level to maximize throughput. Note that complexity may be avoided if the source fluid 150 is arranged such as to maintain a desired TMP at the filter 160 without the need of a pump 190 or pressure sensor 162. For example, the source fluid 150 may be provided by a batch container elevated at a certain height to provide a desired head. Note that a control valve 165 or a speed of the pump 190 may be used to regulate the flow rate to maintain desired TMP limits.

A control/shutoff valve 180 may provide the controller 170 the ability to stop the flow of fluid through the filter 160 once a desired volume is reached. A heater 185 may be provided to warm the sterile replacement fluid 130 to prepare it for use. An insulated container 145 may be used to reduce heat loss so that heater 185 can be a relatively low power type. The heater 185 may be controlled by the controller 170 to ensure the replacement fluid 130 is at a desired temperature when required to be used. Alternatively the heater 185 can be controlled by an independent device actuated by, for example, a pressure sensor (not shown) triggered by the flow of fluid into the batch container 147, a timer (not shown) settable to trigger based on a predefined treatment time, or some other means. Preferably, in either case, a temperature regulator (e.g., a temperature sensor 183 combined with logic in controller 170) regulates power to the heater to ensure a required temperature is maintained and not exceeded. The temperature sensor 183 may be used to sense the quantity of sterile replacement fluid by the rate of detected temperature increase versus heater output. The temperature sensor 183, heater 185, and sterile replacement fluid 130 can be modeled in any desired fashion. For example one may neglect all but the thermal mass of the RF, assume perfect heat transfer (including assuming the RF fluid to be isothermal). Then, the mass would be given by the product of the temperature change, the thermal capacitance of the fluid, and the heat output rate of the heater. More complex theoretical or empirical algorithms would be a simple matter to derive and implement. Once the mass of fluid is calculated to be below a certain level, the controller 170 may be programmed to respond in accord with the assumption the sterile RF is exhausted. Equivalently, the controller 170 may simply respond to some predefined rate of temperature rise of the temperature sensor 183.

When the temperature of the sterile replacement fluid 130 is raised, dissolved gas may come out of solution. This may cause bubbles to accumulate inside the replacement fluid container 247, which is undesirable because of the risk of infusing bubbles into the patient's bloodstream. To help ameliorate that problem, a vibrator or ultrasonic transducer may be provided 183 to cause bubbles to coalesce and rise to a top of the container 147. As a result, bubble-free replacement fluid may be drawn through the outlet 148.

A connector 195 may be provided for connecting the source fluid to the line 120. The connector may be a luer, spike, threaded adapter, or any other suitable type. Although the various controls indicated above are shown to be controlled an automatic controller 170, each may be controlled also by manual mechanisms.

The FIG. 1 embodiment allows replacement fluid to be prepared in batch for later use. Thus, the rate of filtration of replacement fluid need not match the requirements of the treatment process or preparatory steps such as priming. As a result, a low capacity filter may be used for the filter 160. For example, typically only a small quantity of expensive media is required to make a small-capacity filter and as such, the cost of a low capacity filter can be much smaller than a high capacity filter.

Also, other features found in high capacity filters, such as a large ratio of media surface to volume of the filter module are achievable only by means of folding or forming media into shapes that can be difficult to manufacture, such as tubes. Thus, savings can be achieved in simplification of the configuration of the filter as well. Relatively small filters with simple planar media held in plastic casings are available and suitable for this purpose.

The configuration of FIG. 1 may be retrofitted for use with an existing treatment system. For this purpose, the outlet 148 may provide with any required connection adapter. A user interface 175 for entering data into the controller 170 may be provided as well.

Figure 2:
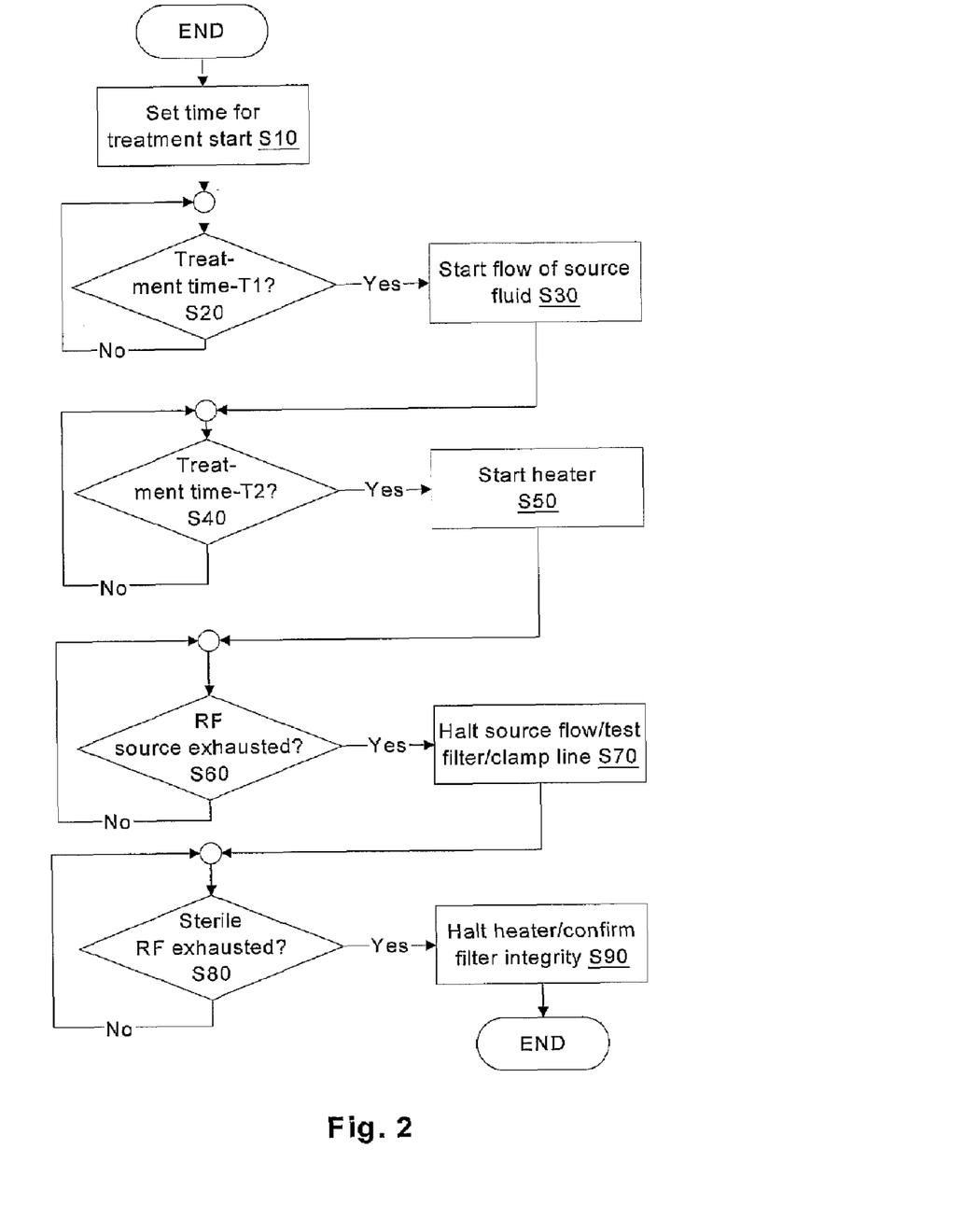
FIG. 2 is a flow chart illustrating an exemplary control procedure applicable to various embodiments of the invention including those of FIGS. 1 and 3.

Referring now to FIG. 2, a control algorithm for controlling the heater 185, pump 190, valves 165/180, etc. begins with the a setting of a time for treatment S10, for example by entering a time into the controller 170 via a user interface (UI) 175. The time can be entered manually or automatically by means of, for example, a data signal from a remote source via a switched or network circuit. The time for treatment may be obtained from a treatment calendar entered into the controller 170, which also may be obtained from a remote source. In the present simple algorithm, first and second time intervals T1 and T2 are defined representing the interval required for filtration of RF and the interval required for heating of RF, respectively.

These values may be obtained from any of the above means (e.g., local manual or remote entry via UI/interface 175) or from data encoded on one of the consumables involved in the process. For example, the filter 160, the RF fluid container 147, the source fluid 150 container (s), or any other consumable may be provided with one or more bar-codes, RFID tags, or other suitable encoding device. Such devices may provide values for T1 and T2, tables of values that depend upon other factors, or other data from which T1 and T2 may be derived.

The controller 170 waits until it is time to start the flow of raw RF fluid from source fluid 150 toward container 147 by comparing a current time (indicated by a clock internal to the controller 170, which is not shown) to a difference between a scheduled treatment time and T1, which represents the lead time (ahead of the scheduled treatment) required for the filtering process. A loop through step S20 is exited to step S30 when the clock reaches the treatment time minus T1. At step S30, the flow of source fluid 150 through the filter 160 is initiated. If the pump 190 is present, it may be started and regulated according to a specified TMP. The latter may be provided to the controller 170 manually or automatically through UI/interface 175. Automatic entry may be by way of a data store such as bar-code or RFID attached to the filter, for example which may be read when the filter 160 is installed in a chassis with a corresponding reader device (not shown). Note, as mentioned above, the source fluid may be sterile and the filtration process provided as a guarantee against contamination, for example by accidental touching.

Once the flow of source fluid 150 is initiated, the controller waits for the required time for applying power to the heater 185. The delay and the initiation are controlled by step S40 which is exited to step S50 only when the treatment time minus the predefined interval T2 is reached. As mentioned above, alternatively, the heater may be triggered by detecting fluid such as by means of a sensor (not shown) triggered by the presence of sterile replacement fluid 130 in the container 147. The sensor may be any of a variety of types, such as an ultrasonic sensor, capacitance sensor, mass sensor, optical sensor, etc.

Once the heater is started, the controller 170 may wait for the source fluid to be exhausted at step S60. Step S60 exits to step S70 when the source fluid is determined to be exhausted. The latter may be detected by integrating the flow rate to measure the total volume (the rate may be determined by the pumping rate, for example, or by a flow meter (not shown)). The exhaustion of the source fluid 150 may also be indicated by a quantity indicator (e.g., a level indicator) in the sterile replacement fluid container 147 or an intermediate container supplied through a drip chamber, for example. Alternatively, the exhaustion of the source fluid 150, if supplied from a fixed-volume container, may be indicated by a sensor such as an ultrasonic sensor, capacitance sensor, mass sensor, optical sensor, a scale, etc. Yet another alternative is to sense gas or a precipitous rise in negative pressure (sensed by a pressure sensor which is not shown) at the pump 190 inlet. At step S70, the line 120 may be clamped by actuating shutoff/control valve 180. Additionally, if appropriate, the pump 190 may be deactivated at the point where the exhaustion of the source fluid 150 is detected at step S70.

According to an embodiment, as the fluid is pumped, the TMP of the filter, as indicated by pressure sensors 162, may be monitored. If the TMP is determined by the controller 170 to be, at any point, below a predetermined nominal value or to have changed precipitously during filtration, the controller 170 may trigger an alarm or take some other action to insure that the resulting replacement fluid is handled appropriately. For example, a back-up filter could be added during treatment as discussed with respect to FIG. 5. The TMP results could trigger an alarm at any point during filtration or could be assessed and reported at step S70, before treatment would begin.

The controller 170 pauses again at step S80 to wait for the sterile fluid to be exhausted. This may be indicated by a signal from the treatment machine (e.g., received via UI/interface 175) or by direct measurement by a sensor, such as an ultrasonic sensor, capacitance sensor, mass sensor, optical sensor, a scale, etc. As mentioned above, the controller 170, or the heater 185 itself, may be provided with a threshold temperature-rise rate that indicates the mass of fluid in the replacement fluid container 147 has fallen below a minimum level. The loop of step S80 is exited to step S90 where power to the heater 185 is terminated.

Note that all the functionality attributed to the controller 170 may be provided, via a control interface, by a controller (not shown) internal to a treatment machine. For example, the apparatus of FIG. 1 could be provided as an optional module for such a treatment machine rather than a retrofit module.

Figure 3:
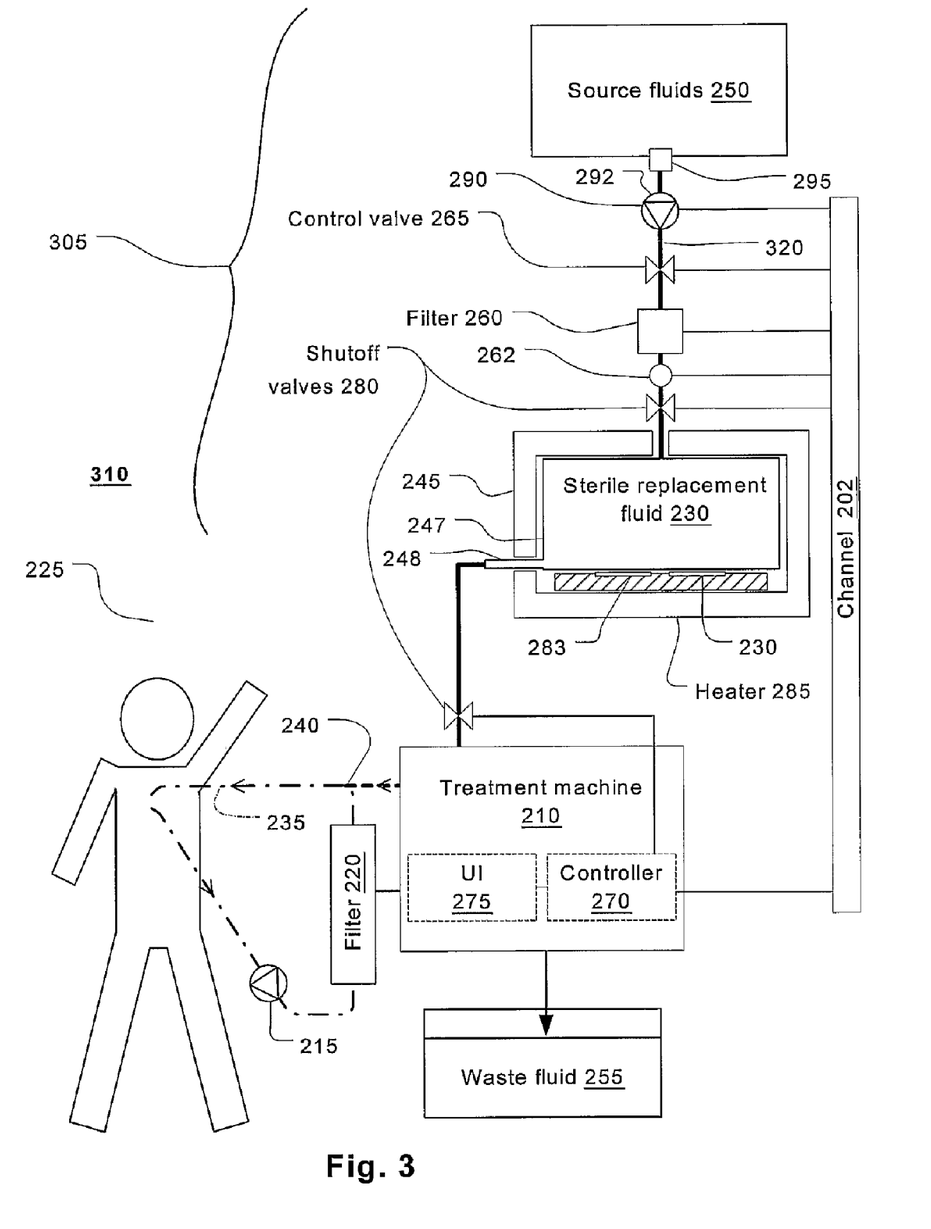
FIG. 3 is a schematic illustration of a blood treatment machine with an attached subsystem for batch preparation of sterile replacement fluid.

Referring now to FIG. 3, a combination blood treatment system and sterile replacement fluid device 310 has a replacement fluid preparation subsystem 305 configured substantially as the device of FIG. 1. A filter 260 filters fluid from a source of fluid 250 to generate a batch of sterile replacement fluid 230 as in the embodiment of FIG. 1. Again, the source of fluid 150 may be a container of sterile or non-sterile replacement fluid, one or more containers of constituents which, when combined, form a proper replacement fluid and any of the latter may include a continuous source such as a water tap. A line 220 conveys the source fluid 250 through the filter 260 and into a batch container 247, which may be any type of sterile, preferably disposable container, for example, a large IV bag. It may also include a number of such containers appropriately interconnected to permit flow into and out of them in the fashion of container 247.

Again, a pump 290 may be provided and pressure at an outlet of the filter 260 may be sensed by a pressure sensor 262. The pump 290 may be controlled by a controller 270 to insure a maximum safe TMP to maximize throughput. Again, the pump 290 is not required and the source fluid 150 may be arranged such as to maintain a desired TMP at the filter 160 without the need of the pump 290 or pressure sensor 262 by elevation. A control valve 265 or a speed of the pump 290 may be used to regulate the flow rate to maintain desired TMP limits.

A control/shutoff valve 280 may provide the controller 270 the ability to stop the flow of fluid through the filter 260 once a desired volume is reached. A heater 285 may be provided to warm the sterile replacement fluid 130 to prepare it for use. An insulated container 245 may be used and the heater controlled as discussed with respect to the FIG. 1 embodiment. Bubbles may be controlled, as discussed above, by means of a vibration or ultrasonic transducer 230 as discussed above with regard to the previous embodiment.

A connector 295 may be provided for connecting the source fluid to the line 220. The connector may be a luer, spike, threaded adapter, or any other suitable type. Although the various controls indicated above are shown to be controlled an automatic controller 270, each may be controlled also by manual mechanisms. Other aspects of the control mechanisms for the embodiment of FIG. 3 may be provided as discussed with respect to FIGS. 1 and 2.

The benefits of the FIG. 2 embodiment are similar to those of the FIG. 1 embodiment in that it allows replacement fluid over a time period that is not driven by the speed of supply to the treatment process. As a result, a low capacity filter may be used for the filter 260 with the attendant benefits identified above. Note that the UI/interface 275 and controller 270 are shared in the present embodiment by the treatment machine. Thus, any information required for control of both the treatment and preparation of sterile replacement fluid 230 would not need to be communicated to a separate controller such as controller 170. Note also that the communications among the illustrated components is provided by a channel 202 which may be wire harness, separate wires, a bus, a wireless channel or any suitable communications/power transmission device.

In the embodiment of FIG. 3, a predicted quantity of replacement fluid may be filtered and stored for use during treatment. If, however, for some reason, more is required, the treatment machine controller 270 could be configured to identify that situation and control the subsystem 305 components to provide it. Many blood treatment process employ a filter 220 to filter blood and into which replacement fluid is supplied to a patient 225. More details on preferred embodiments of the treatment machine are discussed below.

In either of the above embodiments, the rate of flow of fluid during preparation of the batch of replacement fluid may be substantially less than the rate of consumption during treatment. In an exemplary embodiment of an application for hemofiltration, the amount of replacement fluid consumed is between 9 and 18 l. and the rate of consumption is approximately 200 ml./min. Also, the media used for sterile filtration may be any suitable media that insures the quality of the replacement fluid is as desired. In the embodiments discussed above, it was assumed that the end sought was preparation of sterile replacement fluid employed microfiltration to prevent the passage of pathogens. However, the invention could be used with other types of filtration or treatment processes to produce a batch of fluid consumed by a medical treatment process, for example, dialysate for hemodialysis treatment. The benefits accrue in particular when the time scale of preparation may be longer than the time scale of consumption.

Moreover, the benefits are more appreciable when some sort of energy-consuming process is required, such as heating, before consumption.

Here, not only is the time scale of preparation compatible with a small inexpensive filter, but the long time scale permits heating of the replacement fluid over a long interval. To support this benefit, the batch container may be insulated to minimize heat loss so a small heater will be adequate. Also, the preferred application for the present invention is in the context of hemofiltration because the quantity of fluid required for such treatment is relatively small.

Note that other motivations for filtering the fluid, in addition to or as an alternative to sterilization of a non-sterile fluid, is (1) removal of air bubbles and/or (2) as a safety net for ensuring against accidental contamination. If bubble removal is the only concern, a drip chamber may be used instead of a filter. For removing bubbles, the filter preferably is of a type that permits the passage of fluid, but which blocks the passage of bubbles, for example due to its media pore size and the surface tension of the fluid.

Figures 4A, 4B:
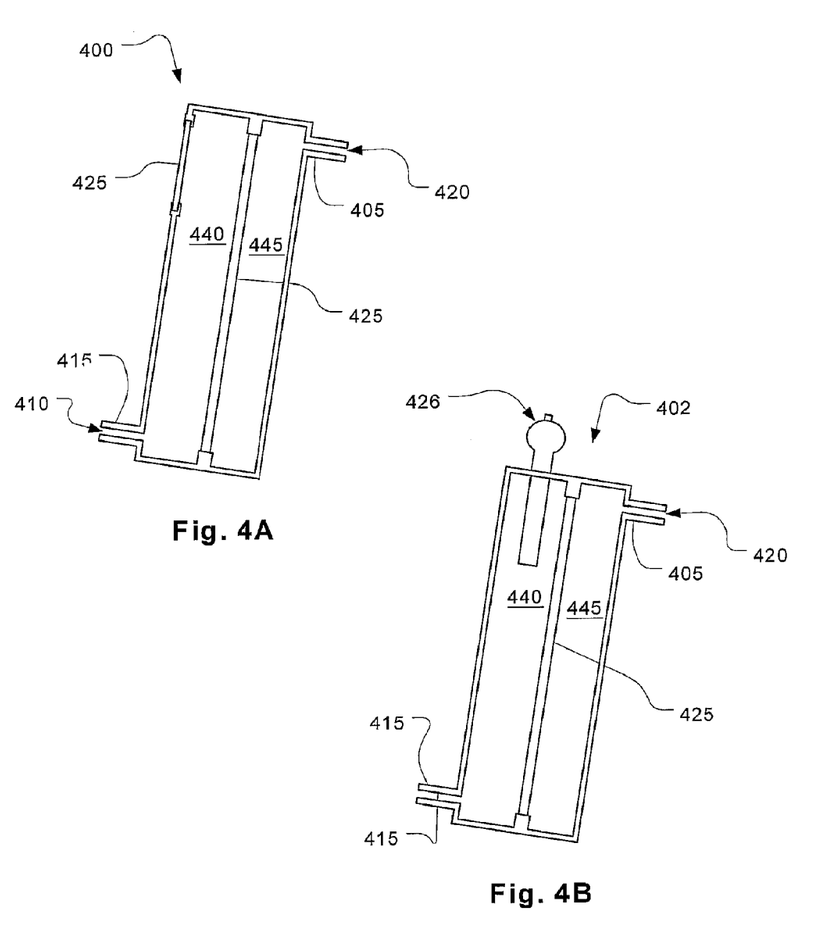
FIGS. 4A and 4B are illustrations of fluid filters that may be use in various embodiments of the invention.

Referring now to FIG. 4A, a preferred type of filter for some of the present embodiments has an inlet port 415 providing an inlet channel 410 communicating with an inlet chamber 440. An outlet leading port 405 provides an outlet channel 420 communicating with an outlet chamber 445. A piece of filter media 425 separates the inlet and outlet chambers 440 and 445. The fluid to be sterilized enters the inlet chamber 440, is sterilized by passing through the filter media 425, and exits via the outlet chamber 445. A gas relief gasket 425 allows gas accumulating in the inlet chamber 440 to be released to the ambient atmosphere.

Internal supports and structural details are not shown in the illustration for clarity, but a practical embodiment of the filter of FIG. 4 may have ribs for strength and internal supports for the media 425 and gasket 425 so that the filter 400 may be capable of tolerating a substantial TMP.

The gas relief gasket 425 may be of a porous hydrophobic material such as PTFE. Air bubbles trapped in the inlet chamber 440 can coalesce in the inlet chamber 440 and exit via the air relief gasket 425. It may be, depending on the type of gas relief gasket 425 used, that a substantial TMP will be required to eliminate air.

An alternative to the gas relief gasket 425 is a gas relief valve 426 as shown in FIG. 4B. Since the inlet chamber 440 is connected to the non-sterile side of the filtration system, there is little risk of contamination if microbes were to enter through a mechanical device such as the gas relief valve 426. The latter is illustrated figuratively and allows only gas to escape. Other features of the embodiment of FIG. 4B are labeled with the same numerals as features of the embodiment of FIG. 4A where they serve substantially identical functions and, thus, their descriptions are not repeated here.

Figure 5:
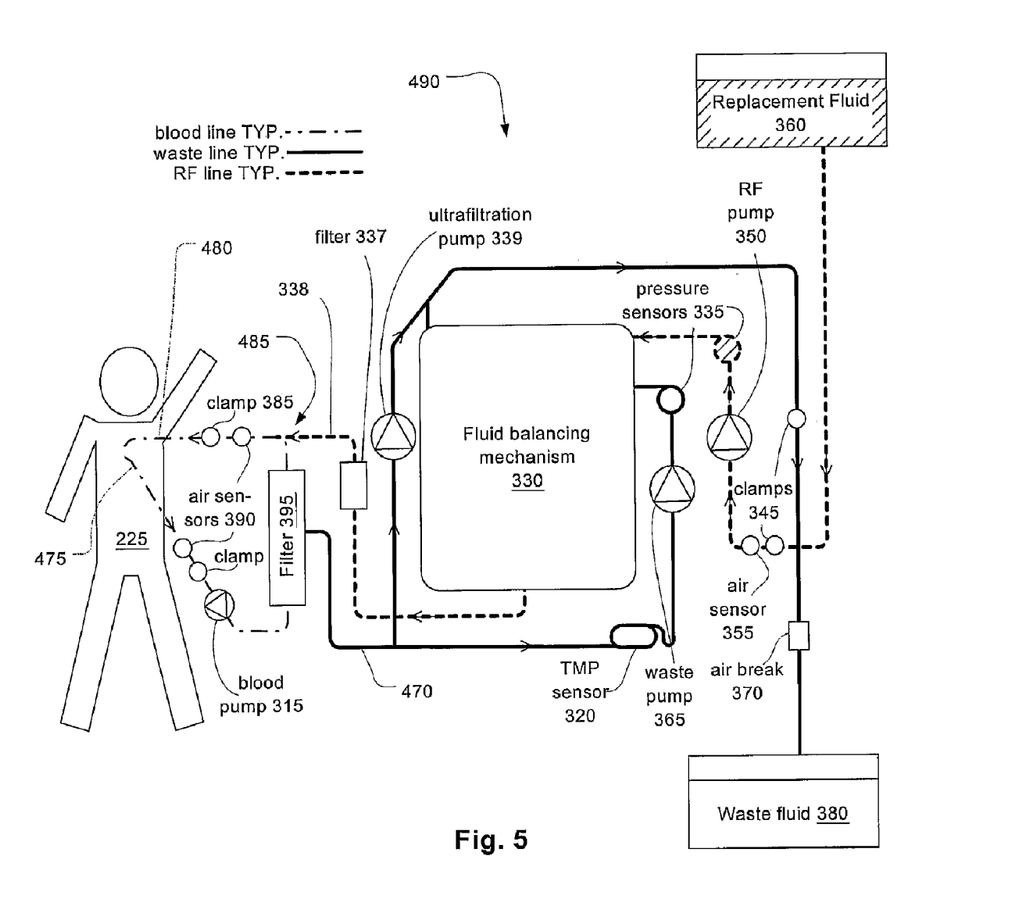
FIG. 5 illustrates an exemplary blood treatment system with a filter used to sterilize and/or degas replacement fluid during treatment.

Referring now to FIG. 5, the filters of FIGS. 4A and 4B may be used for filtration of replacement fluid in the embodiment of FIG. 5 as discussed presently.

Replacement fluid 360, which may or max-not be sterile, is supplied to a hemofiltration machine 490. A replacement fluid pump 360 pumps the replacement fluid into a balancing mechanism 330 which meters the replacement fluid before it is introduced, via a junction 485, into the venous (return) line 480 and ultimately into the blood stream of a patient 225. Waste fluid is drawn through a waste line 470 from a filter 395 and pumped via a waste pump 365 through the fluid balancing mechanism 330. The fluid balancing mechanism 330 meters the replacement fluid to match the rate of withdrawal of waste fluid so that the patient's fluid balance is maintained during treatment. Actually, the rate of withdrawal of waste fluid may be less than the rate of metering of replacement fluid by pumping waste fluid through a bypass pump called an ultrafiltration pump 339. The latter sends some of the waste fluid directly to a waste fluid sump 380, thereby bypassing the fluid balancing mechanism 330. The fluid balancing mechanism is depicted figuratively and may operate in accord with any suitable control device. Preferably it meters replacement fluid on an equal-volume or equal-mass basis. A preferred mechanism is described in U.S. patent application Ser. No. 09/513,911, filed Feb. 25, 2000, now U.S. Pat. No. 6,638,478 entitled: "Synchronized Volumetric Fluid Balancing Systems and Methods," which is hereby incorporated by reference as if fully set forth in its entirety herein. Various sensors and line clamps, Indicated figuratively 335, 355, 320, 385, and 390, may be provided to control flow and ensure safe operation.

A filter 337, is provided in the replacement fluid line 338 just upstream of the junction 485. The filter 337 may serve as a last chance safety net for ensuring that replacement fluid is sterile and/or that all bubbles are removed before flowing into the venous line 480. To ensure that air is not infused into the patient's body, an air sensor 390 is often provided in hemofiltration systems, but detection of air normally triggers an alarm, automatic shutdown, and skilled intervention to restart the hemofiltration treatment. Obviously, this is undesirable so the system should, as effectively as possible, insure that air or other gas is not injected into the venous line 480.

Although in the embodiment of FIG. 5, a hemofiltration machine was discussed, other types of treatment processes may be provided a last-chance filter similar to filter 337. For example, hemodiafiltration, hemodialysis, or other treatments may require the infusion of replacement fluid and thereby benefit from a filter such as filter 337. Preferably, the filter 337 is substantially as in the embodiment of FIG. 4A. Thus, the filter 337 removes both air and pathogens.

Instead of employing a filter at the location indicated at 337, a drip chamber may be used. Suitable drip chambers are currently available with air vents and microfilters effective to remove pathogens, so they may be substituted for the filter 337. Also, in some cases, it may be that there is very little risk that the replacement fluid is contaminated with pathogens, the filter 337 may serve as a mechanism for removing only air or other gases. In such cases, drip chambers which remove gas (either with or without a vent), could be employed at the above location in the fluid circuit.

Figure 6:
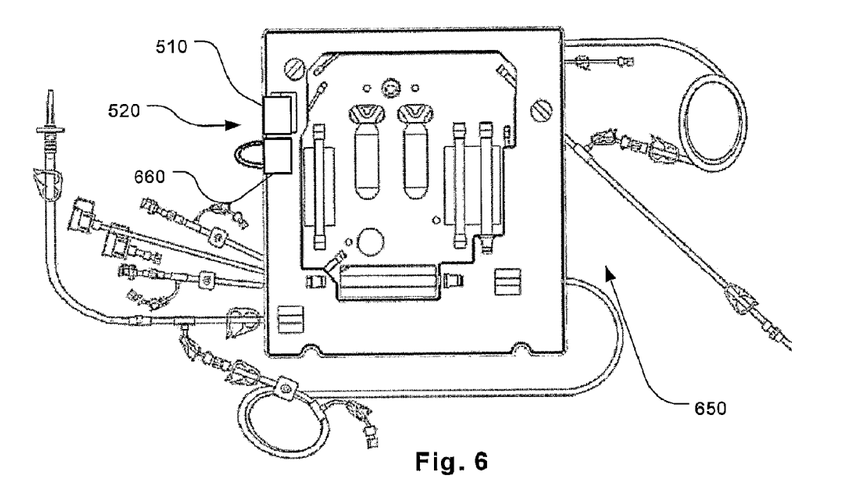
FIGS. 6-8 illustrate a blood treatment machine and cartridge providing various supporting mechanical features for the embodiment of FIG. 5 and further embodiments, including one in which a quality of replacement fluid is sensed before infusion.
Figures 7, 8:
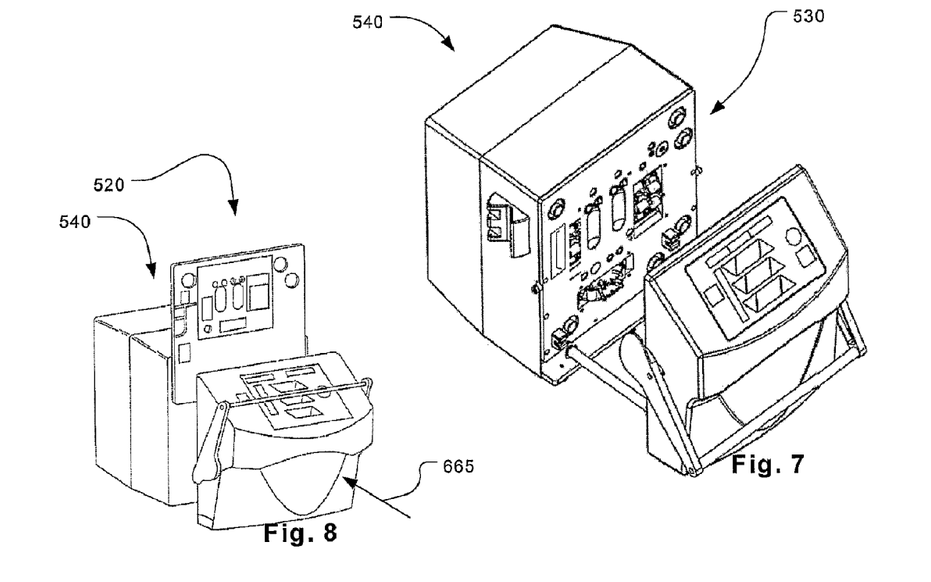

Referring now to FIGS. 6, 7, and 8 the last chance filter or drip chamber (or combination device) 510 may be installed in a cartridge 520 that holds and orients blood and fluid circuits for a hemofiltration machine 540. In the embodiment shown, which is described substantially in U.S. patent application Ser. No. 09/513,773 filed Feb. 25, 2000, now U.S. Pat. No. 6,579,253 and entitled: "Fluid Processing Systems and Method Using Extracorporeal Fluid Flow Panels Oriented Within A Cartridge," hereby incorporated by reference in its entirety as if fully set forth herein, fluid circuit components may be held in a cartridge 520 and clamped (as shown in FIG. 8 with the machine closing as illustrated by the arrow 665) within receiving gap 530 in a blood treatment machine such as hemofiltration machine 540. The cartridge 520 may have a preferred orientation which may insure correct orientation for the last chance filter or drip chamber (or combination device) 510 if required by the particular device chosen. To insure orientation of the last chance filter or drip chamber (or combination device) 510, the latter is preferably held by the cartridge 520 in a fixed orientation with respect to the cartridge 520.

In an alternative embodiment, the last chance filter or drip chamber (or combination device) 520 may be accompanied by a device 660 for measuring the quality of the replacement fluid, such as conductivity or density. This may provide a last-chance check that the replacement fluid is of the correct type. For example, where such fluids are derived from mixtures, if the proportion is not exactly what is required, infusion could be harmful to the patient 225. An example of a device 660 to test the fluid could be a wettable pair of contacts (not shown) formed in a tubing set 650 of the cartridge may be used in conjunction with a resistance measurement device to measure the ion concentration of the fluid. Alternatively, a non-wettable sensor, such as an ultrasonic conductivity cell could be used. Other kinds of fluid quality sensors could be employed such as new types of specific-molecule detectors built on silicon wafers.

Preferably, the tubing set 650 and cartridge 620 of which it is a part form a disposable component that is used for one treatment and disposed of. Note that the fluid quality sensor 660 may used alone or together with the last chance filter or drip chamber (or combination device) 510. Note, although FIGS. 6 and 7 are detailed, they are intended to show various components figuratively and do not reveal the details of the routing necessary to achieve the flow paths discussed with respect to them or as illustrated elsewhere.

Figure 9:
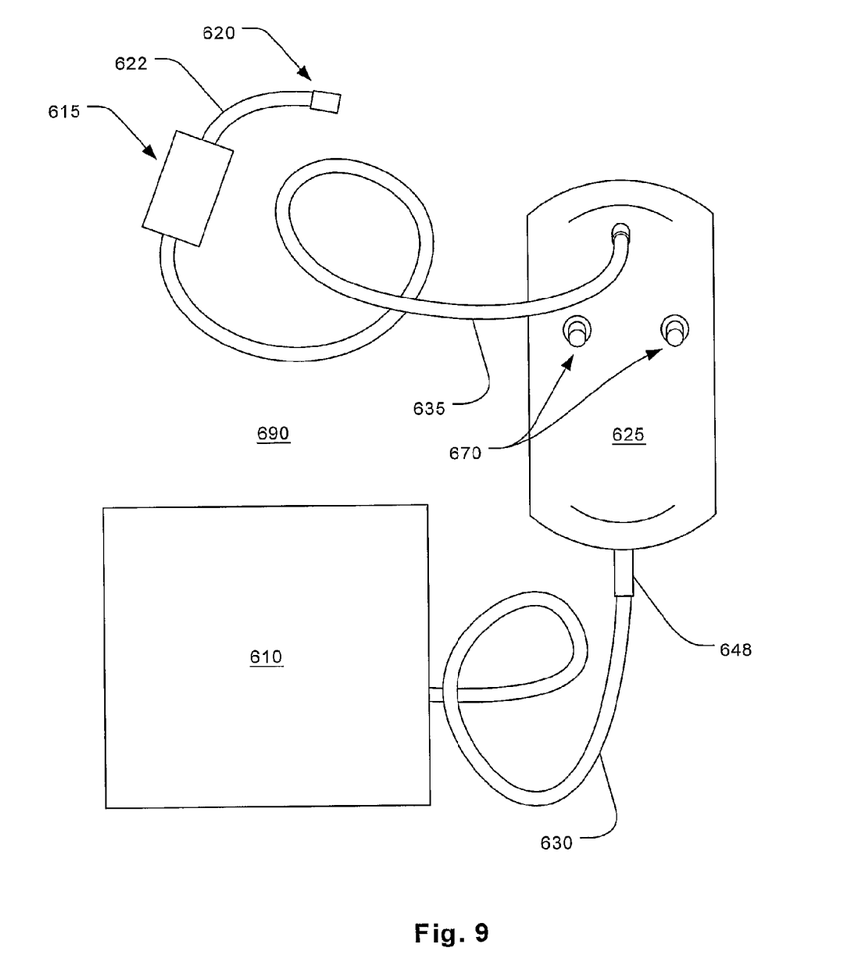
FIG. 9 illustrates a disposable fluid circuit kit which may support various embodiments of the invention.
Figure 10:
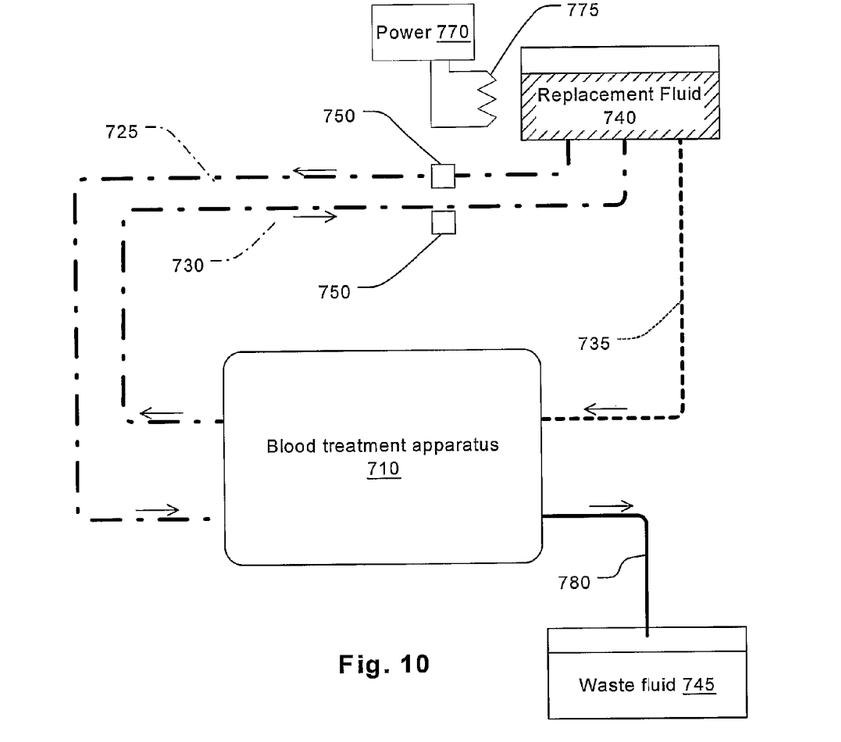
FIG. 10 illustrates a set up for priming a blood treatment process, which components of the invention may be used to support.

Referring now also to FIG. 9, the tubing set and cartridge assembly 610, discussed previously, may incorporate the batch replacement fluid container 625 as part of a sterile replaceable set 690. The filter 615 may have a tube 622 with a connector 620 for attachment to a source fluid 250. A tube 635 may connect the filter to the batch replacement fluid container 625, which may he fitted with another tube 630 to convey fluid to the tubing set and cartridge assembly 610. Referring now also to FIG. 10, the batch replacement fluid container 625 may also be fitted with additional connectors 670 and/or extensions (not shown) to permit the batch replacement fluid container to be used for priming blood, replacement fluid, and/or waste lines. For example, as discussed in U.S. patent application Ser. No. 09/905,246, filed Jul. 12, 2001,now U.S. Pat. No. 6,649,063 entitled: "Devices and Methods For Sterile Filtering of Dialysate," which is hereby incorporated by reference as if fully set forth in its entirety herein, replacement fluid is circulated through a replacement fluid container 740 to flush air out of all the fluid circuiting (not all shown)of blood treatment apparatus 710. As described in detail in the '246 application incorporated by reference above, the venous (return) and arterial (supply) blood lines 725 and 730 may be temporarily connected via connectors 750 to the replacement fluid container 740 and fluid circulated through the container 740 until gas bubbles are substantially purged from the relevant circuits. Note, the replacement fluid container 740 corresponds to the containers 147

Note, the replacement fluid container 740 corresponds to the containers 147 (FIG. 1), 247 (FIG. 3), and 625 (FIG. 9) in the foregoing figures and to respective containers in the application incorporated by reference immediately above. The air and other gases may settle in the replacement fluid container 740 as the fluid circulates. Liberation of the gases would ordinarily be promoted by the application of heat from a heater 775 (with power source 770), which may be employed as discussed with regard to the embodiments of FIGS. 1-3 or in any suitable way to bring the temperature of the replacement fluid to body temperature. Replacement fluid circuits including line 735, blood circuits including lines 725 and 730, and waste fluid circuits including line 780 may all be flushed with fluid from the container 740. The details of the blood treatment apparatus and its internal plumbing can vary. Replacement fluid may be transferred from the replacement fluid line 735 or from the blood line 735 to the waste line, for example through a filter, to flush the waste portion of the circuit including the waste line 780. Replacement fluid may circulate through the blood circuit including lines 725 and 730 as indicated to flush the blood circuit, at least a portion of which may be closed as indicated by the arterial and venous lines 730 and 735.

Disposable components, such as the circuit sets of FIGS. 8 and 9 or the batch replacement fluid container 625 alone, or other components that may be used with the embodiments disclosed may be packaged with instructions for preparing infusible replacement fluid. For example, the source fluid 150/1250 or a concentrate which may be mixed to make the same (FIGS. 1 and 3) may be supplied with instructions for sterile filtering the fluid as described in the instant specification. Such may constitute packages of consumables or reusable components.

Note that benefits of the filtering method and apparatus discussed above may best be achieved by performing the filtration just prior to treatment, although this is not required. The filtering method may be performed at the treatment site. For example, non-sterile concentrate may be stored at the residence of a patient.

The concentrate may be diluted with distilled water in a source fluid container (e.g., 196 of FIG. 1) at the residence and processed as discussed in the instant application.

Because the infusible fluid is generated at the treatment site, the need for regulatory-cleared fluids, such as might be obtained from a manufacturer, is not avoided. Cost savings and storage-space economies can thus be realized by the patient. This is particularly important in view of the fact that renal replacement therapies are often administered many times per week and storage and cost of consumables can present a serious problem in a residence or any other facility.

Figure 11:
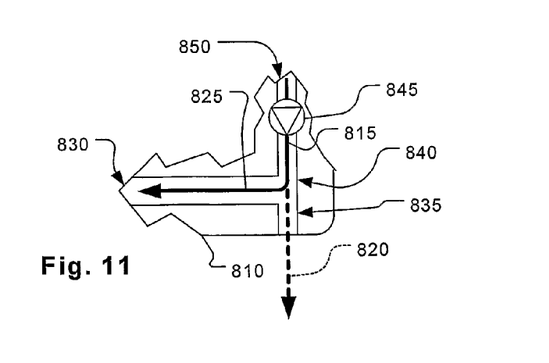
FIG. 11 illustrates a portion of a blood treatment machine that allows a pump used as part of the blood treatment to also be used to control the filtering of fluid to provide a batch of infusible replacement fluid.

Referring now to FIG. 11, a blood treatment machine, a portion of which is illustrated figuratively at 810, may permit a pump 845 that, during treatment, conveys replacement fluid to a patient, to be used for filtering a sterile filtering a non-sterile source fluid. Here, the machine 810 has a common guide 850 that accommodates a fluid line 815 through which fluid is conveyed by the pump 845, for example a peristaltic pump. During treatment, the line 815-825 may be guided by a first selected guide 830 in a first direction toward other components of an internal fluid circuit (not shown) as indicated at 825. During sterile-filtering, fluid may be pumped by the same pump 845 through a line 815-820 that is allowed to pass out of the blood treatment machine 810 via a different guide 835. This allows the line 815-820 to be fed to an external connection to the sterile fluid container (not shown) as indicated at 820.

Figure 12:
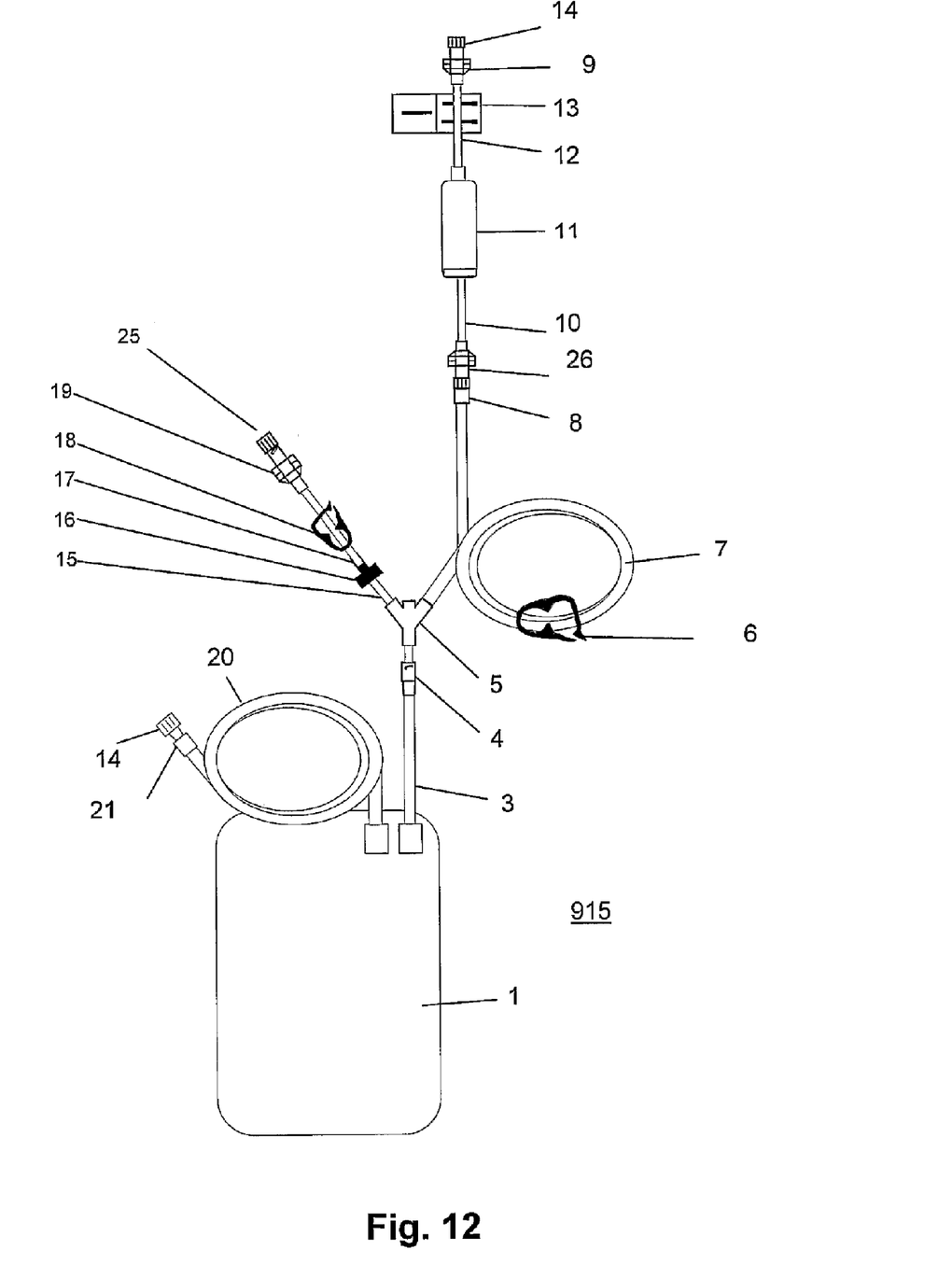
FIG. 12 illustrates replacement fluid container tubing set.

Referring now to FIG. 12, another embodiment of a replacement fluid container portion of a disposable tubing set includes a replacement fluid container 1, a break-off female luer lock connector 4, a y-connector, 5, a pinch clamp 6, a male luer 8, a female luer 26, a 0.22 micron pore anti pyrogen filter 11, a non reopenable tubing clamp 13, a non-breathing cap 14 on a female luer 9, an in-line check valve 16, a pinch clamp 18, a break-off male luer cap and female luer 19, and a female luer 21 and tubing branches 3,7, 10,12, 15,17, and 20. The replacement fluid container 1 is delivered to a patient treatment setting as a sealed sterile container with all terminals sealed. The replacement fluid container contains, as delivered, a concentrate solution sufficient to create a treatment batch of replacement fluid when water is added.

Concentrate may be added by means of the luer connector 21. In the deliverable to the treatment site, the tubing branch 20 may be sealed and cut after the concentrate is added. Water is added at the treatment site through connection to a water source via luer 19. The water is preferably metered to provide a predefined quantity. The 0.22 micron filter is sufficient to protect against contamination before water is added to the replacement fluid container 1. A sample of diluted replacement fluid may be drawn through the luer 19 before treatment. The check valve 16 prevents any contamination due to backflow from the sampling procedure. After water is added to the replacement fluid container 1, the luer 9 is disconnected from the male luer 8 and the male luer connector connected to the blood treatment system.

Figure 13:
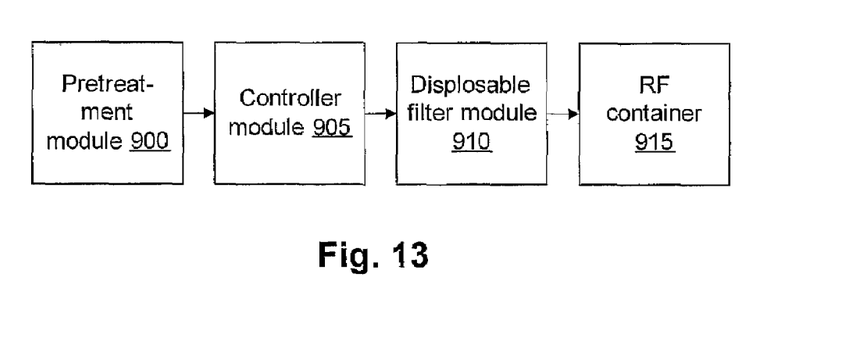
FIG. 13 illustrates a replacement fluid preparation apparatus.

To supply suitable water that is substantially free of unwanted dissolved and undissolved materials, a combination of permanent and replaceable components may be provided at the treatment site. FIG. 13 illustrates such a set up in overview fashion. A pretreatment module 900 provides primary filtration from a raw water supply, for example tap water and feeds prefiltered water to a controller module 905 which provides various control functions, a pump, pressure detection and control, and permanent filtering capabilities which are not shown separately here. Water is metered by the control module into a consumable disposable module 910 which may provide deionization, adsorption filtration, microporous filtering, chemical pretreatment, etc. and any other types of filtering that may require replacement of components. The purified water is finally conveyed to the replacement fluid container circuit 915 discussed with reference to FIG. 12.

Figure 14:
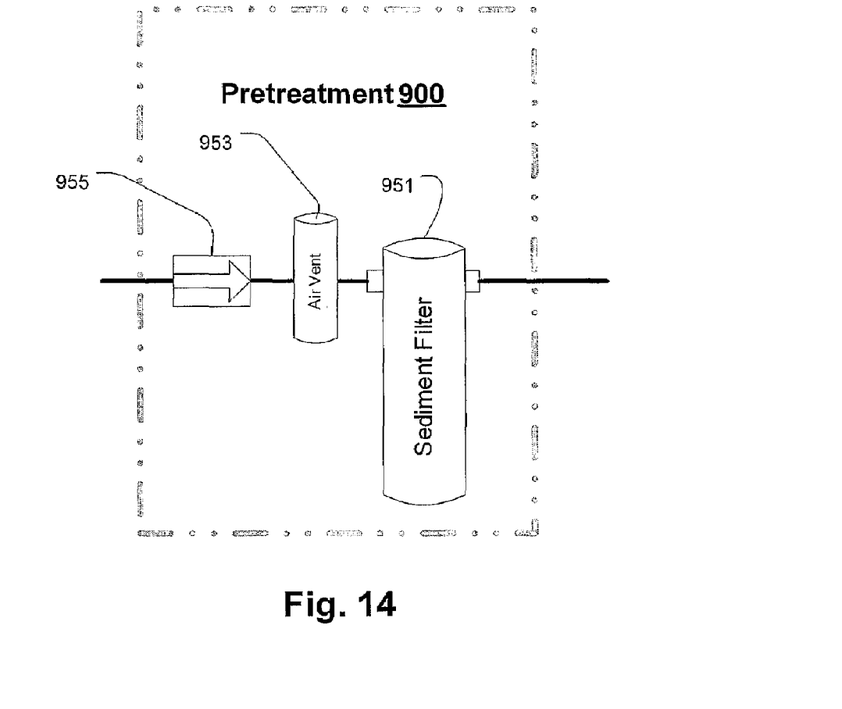
FIGS. 14, 15, and 16 illustrate portions of the replacement fluid preparation apparatus of FIG. 13.

Referring to FIG. 14, pretreatment module 900 is shown in more detail. A check valve 955 prevents backflow. An air vent 953 removes air from the primary supply and a sediment filter 951 (which may be replaceable) provides substantial filtering of solids.

Figure 15:
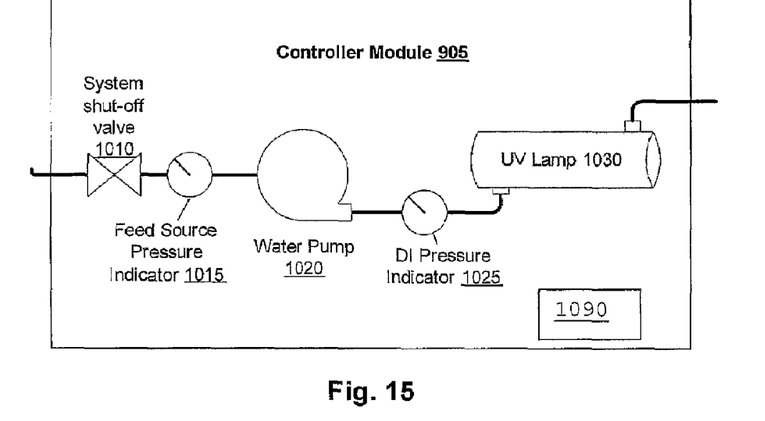

Referring to FIG. 15, the control module 905 is shown in greater detail. A shutoff valve 1010 is provided for safety. Pressure indicators 1015 and 1025 may be provided for monitoring the respective pressures in and out of a pump 1020.

Feedback regulation may be provided to ensure that consistent metering is provided if the pump is relied upon for measuring the total quantity of water supplied to the replacement fluid container 1. A high intensity ultraviolet (UV) lamp 1030 provides a sterilization mechanism. Preferably, the UV lamp 1030 is of such intensity and wavelength as to provide disintegration of chloramines. In a preferred embodiment, the lamp is characterized by a 245 nm wavelength and an output power of 750 mJ/cm2 up to 1500 mJ/cm2 which is sufficient to remove chloramines.

Figure 16:
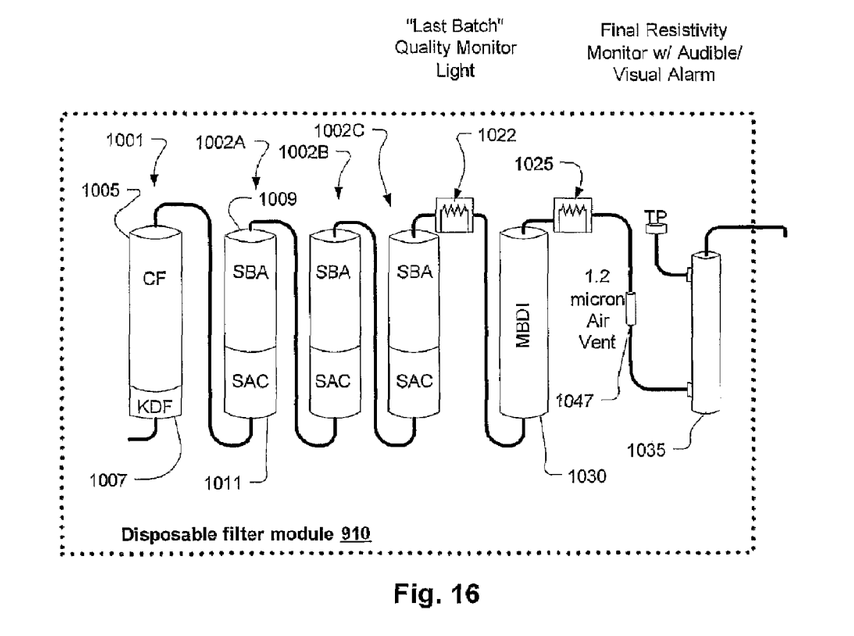

Referring to FIG. 16, the replaceable (disposable or remanufacturable) filter module 910 contains a first stage filter 1007 copper-zinc alloy which is used to subject the water to a reduction/oxidation process to remove ions. This removes ions through a chemical reaction. An embodiment is KDF 85 media where about on pound is used for a flow rate of 150 ml./min water flow rate. A activated carbon filter 1005 follows which is a well-known adsorption type filter. Next threee stages of strong acid cation 1011 and strong base anion 1009 filters follow in series. A sensor

1022 detects ion concentration by contact testing of the conductivity of the water. A signal is generated to indicate that this is the last allowed batch before replacement of the replaceable module 910. A mixed bed deionoization filter 1030 is provided next and a safeguard conductivity test is provided with an audible alarm at 1025 as a back up safety measure. If the conductivity it detects is above a certain level, the pump 1020 may be shut off and an alarm sounded. This may come into play if an operator ignores the tester 1022 which may provide a visual signal or if the tester 1022 fails.

TP is a hydrophobic membrane air vent which allows air in an ultrafilter 1035 to be purged. The ultrafitler 1035 may be a microtubular filter such as used for dialysis. A 1.2 micron air vent may also be provided as shown at 1047.

Note the final conductivity sensor/alarm 1025 may control the pump, as noted. A controller 1090 may be connectable to the disposable filter module 910 and configured to stop the pump 1020. The trigger resistivity safety level to cut-off the pump 1020 may be 1 megaohm, but may be raised to 2 megaohm to allow the use of required temperature compensated resistivity probes (an FDA & AAMI requirement) This does allow use of low cost in-line resisitivity probes in the disposable filter module 910.

The following is a procedure for using the above devices discussed with reference to FIGS. 12-16.

1. Remove the dialysate concentrate tubing set 915 and remove the cap 14 from the tubing line 7 that contains the filter 11. (The 0.22 micron filter 11 provides additional protection from inadvertent contamination.)

2. Connect the water source to the concentrate bag luer connection 9.

3. Break the frangible luer connector 4 which connector is configured
to form a permanent seal on the side facing the Y-junction 5 when disconnected.

4. Add 3 liters of water into the concentrate bag using the purification plant through tubing branch 7 through luer connector 9.

5. Write on the bag label the date and time water was first added to the concentrate bag, to assist in ensuring that it is used within 24 hours.

6. Shake the replacement fluid container 1 well to mix.

7. Confirm solution conductivity prior to use. Remove the break-off cap 1 and draw sample from this branch 16. After removing the sample, clamp the line using the pinch clamp 18 provided.

8. (The following is normative according to a preferred embodiment and not limiting of the invention) Conductivity must be in the range 13.0 to 14.4 mS.

Nominal conductivity for the dialysate solution is 13.7 mS at 25 C. If conductivity does not meet this specification do not use it. Verify that the results are accurate. If conductivity is high additional water may be added to bring it within specification. If conductivity is low then the solution must be discarded.

9. Using the non re-opening clamp 13 provided, clamp the line that is connected to the water purification plant.

10. Using the clamp 6 is next clamped on the line that is connected to the dialysate bagl.

11. Disconnect the water source at the luer connection 26

12. Connect the bag of dialysate solution to the dialysis circuit at the connection 8. This leaves the filter 11 and permanent clamp 13 in place to protect the water supply source.

13. Unclamp the line going to the dialysate bag (red clamp), and initiate treatment after verifying that dialysate will be used within 24 hours from when water was added.

Although the foregoing invention has, for the purposes of clarity and understanding, been described in some detail by way of illustration and example, it will be obvious that certain changes and modifications may be practiced that will still fall within the scope of the appended claims. For example, the devices and methods of each embodiment can be combined with or used in any of the other embodiments.

What is claimed is:

1. A method of administering a renal replacement therapy requiring a sterile fluid, comprising:
    at least one of carbon-filtering, deionizing, and ultra-filtering water to produce a source fluid;
    sterile-filtering the source fluid to generate a sterile fluid;
    flowing the sterile fluid into a sterile batch container;
    the sterile-filtering and flowing being performed at a location and time at which a patient is to be treated;
    the at least one of carbon-filtering, deionizing, and ultra-filtering being performed at the location at which the patient is to be treated; and
    flowing the sterile fluid from the sterile batch container to a treatment system,
    wherein at least one of the sterile-filtering and flowing the sterile fluid into a sterile batch container includes automatically controlling at least one of a flow rate of the sterile fluid and a rate of heating of the sterile fluid responsively to data representing at least one of a treatment start time and a volume of the sterile fluid required for a treatment, and
    wherein the flowing the sterile fluid into a sterile batch container includes unsealing a first connector of a connector assembly of the sterile batch container, the first connector assembly being attached to a second filling port of the sterile batch container and reversibly coupling the first connector to an output port of a supply of the sterile fluid.

2. The method of claim 1, wherein the first connector assembly includes an inline sterile filter effective to isolate the contents of the sterile batch container from ingress of contaminants after the unsealing.

3. The method of claim 2, wherein the flowing the sterile fluid into a sterile batch container includes decoupling a second connector of the connector assembly, inline with the first connector, thereby leaving the inline sterile filter attached to the output port.

4. The method of claim 3, wherein the decoupling includes clamping a line of the connector assembly.

* * * * *